US00PP35934P2

(12) United States Plant Patent
Mathey

(10) Patent No.: US PP35,934 P2
(45) Date of Patent: Jul. 2, 2024

(54) ***SYRINGA* PLANT NAMED 'SMNSPH'**

(50) Latin Name: *Syringa pubescens*
Varietal Denomination: SMNSPH

(71) Applicant: Megan M. Mathey, Holland, MI (US)

(72) Inventor: Megan M. Mathey, Holland, MI (US)

(73) Assignee: SPRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 18/239,910

(22) Filed: Aug. 30, 2023

(51) Int. Cl.
*A01H 5/02* (2018.01)
*A01H 6/00* (2018.01)

(52) U.S. Cl.
USPC ..... Plt./248

(58) Field of Classification Search
USPC ..... Plt./226, 248
See application file for complete search history.

*Primary Examiner* — Susan McCormick Ewoldt
*Assistant Examiner* — Zachariah Allan Kay
(74) *Attorney, Agent, or Firm* — C. Anne Whealy

(57) ABSTRACT

A new and distinct cultivar of *Syringa* plant named 'SMNSPH', characterized by its relatively compact, upright to outwardly spreading and mounding plant habit; moderately vigorous growth habit; freely branching habit; freely and remontant flowering habit; large inflorescences with fragrant purplish pink-colored flowers; and good garden performance.

2 Drawing Sheets

Figure 1:
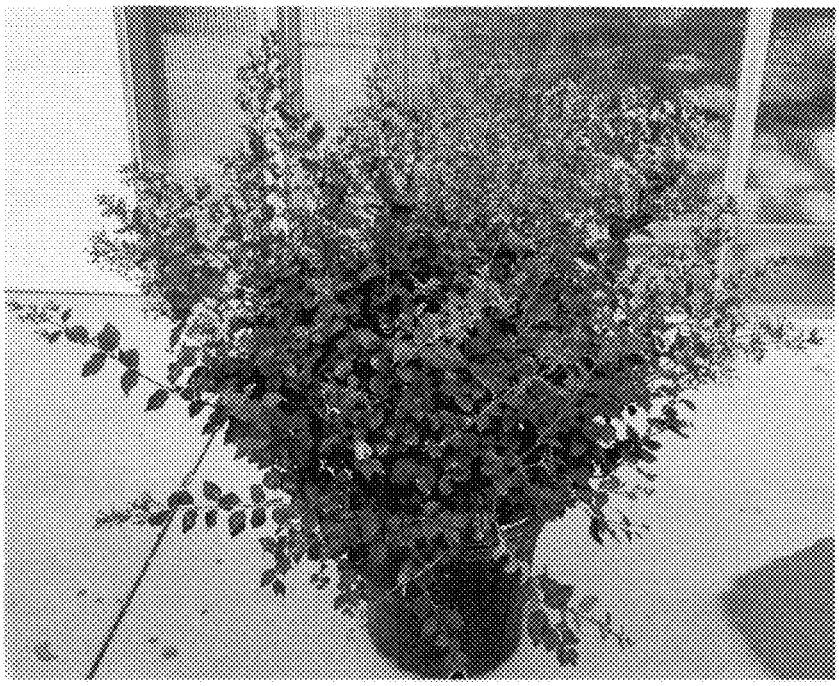

Botanical designation: *Syringa pubescens.*
Cultivar denomination: 'SMNSPH'.

BACKGROUND OF THE INVENTION

The present invention relates to a new and distinct cultivar of *Syringa* plant, commonly referred to as Lilac, botanically known as *Syringa pubescens* and hereinafter referred to by the name 'SMNSPH'.

The new *Syringa* plant is a product of a planned breeding program conducted by the Inventor in Grand Haven, Michigan. The objective of the breeding program is to create new compact and freely-flowering *Syringa* plants with attractive flowers and long remontant flowering habit.

The new *Syringa* plant originated from an open-pollination in 2017 of an unnamed proprietary selection of *Syringa pubescens*, not patented, as the female, or seed, parent with an unknown selection of *Syringa pubescens*, not patented, as the male, or pollen, parent. The new *Syringa* plant was discovered and selected by the Inventor in 2019 as a single flowering plant within the progeny of the stated open-pollination in a controlled environment in Grand Haven, Michigan.

Asexual reproduction of the new *Syringa* plant by softwood cuttings in a controlled greenhouse environment in Grand Haven, Michigan since 2019 has shown that the unique features of this new *Syringa* plant are stable and reproduced true to type in successive generations of asexual reproduction.

SUMMARY OF THE INVENTION

Plants of the new *Syringa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNSPH'. These characteristics in combination distinguish 'SMNSPH' as a new and distinct *Syringa* plant:

1. Relatively compact, upright to outwardly spreading and mounding plant habit.
2. Moderately vigorous growth habit.
3. Freely branching habit.
4. Freely and remontant flowering habit.
5. Large inflorescences with fragrant purplish pink-colored flowers.
6. Good garden performance.

Plants of the new *Syringa* can be compared to plants of the female parent selection. Plants of the new *Syringa* differ primarily from plants of the female parent selection in flowering habit as plants of the new *Syringa* flower more remontantly and for a longer period of time than plants of the female parent selection. In addition, flower color of plants of the new *Syringa* is more vibrant purplish pink than flower color of plants of the female parent selection.

Plants of the new *Syringa* can be compared to plants of the *Syringa* hybrid 'SMNJRPI', disclosed in U.S. Plant Pat. No. 29,802. In side-by-side comparisons, plants of the new *Syringa* differ primarily from plants of 'SMNJRPI' in the following characteristics:

1. Plants of the new *Syringa* are more freely flowering than plants of 'SMNJRPI'.
2. Plants of the new *Syringa* flower more remontantly and for a longer period of time than plants of 'SMNJRPI'.
3. Flower color of plants of the new *Syringa* is more vibrant purplish pink than flower color of plants of 'SMNJRPI'.

1. Plants of the new *Syringa* have larger and denser inflorescences than plants of 'SMNJRPI'.
2. Flowers of plants of the new *Syringa* are lighter purple in color than flowers of plants of 'SMNJRPI'.

BRIEF DESCRIPTION OF THE PHOTOGRAPHS

The accompanying colored photographs illustrate the overall appearance of the new *Syringa* plant showing the colors as true as it is reasonably possible to obtain in colored reproductions of this type. Colors in the photographs may differ slightly from the color values cited in the detailed botanical description which accurately describe the colors of the new *Syringa* plant.

The photograph on the first sheet (FIG. 1) is a side perspective view of typical flowering plants of 'SMNSPH' grown in a container.

Figure 2:
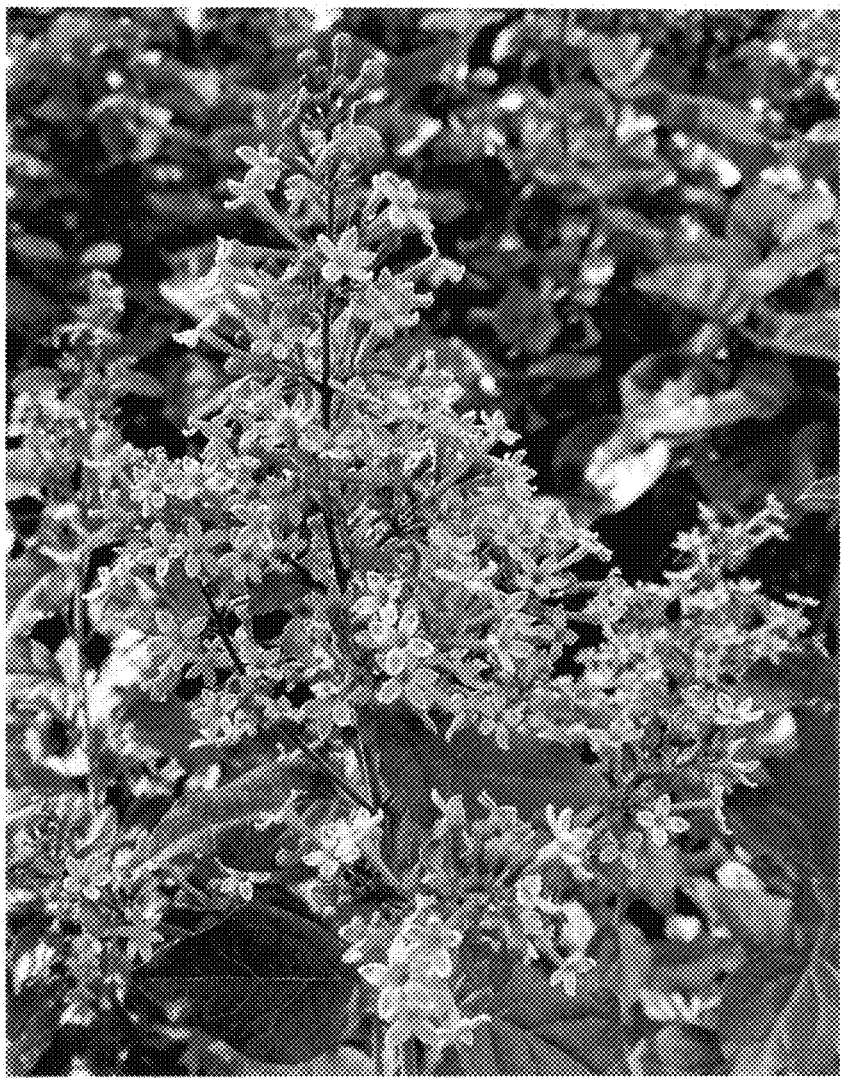

The photograph on the second sheet (FIG. 2) is a close-up view of a typical inflorescence of 'SMNSPH'.

DETAILED BOTANICAL DESCRIPTION

Plants used for the following description were grown during the spring in three-gallon containers in a polyethylene-covered greenhouse and in an outdoor nursery in Grand Haven, Michigan and under cultural practices typical of commercial *Syringa* production. During the production of the plants, day temperatures ranged from 18C to 27C and night temperatures ranged from 5C to 10C. Plants of the new *Syringa* were three years old when the photographs and description were taken. In the following description, color references are made to The Royal Horticultural Society Colour Chart, 2015 Edition, except where general terms of ordinary dictionary significance are used.

Botanical classification: *Syringa pubescens* 'SMNSPH'.

Parentage:

*Female, or seed, parent.*—Unnamed proprietary selection of *Syringa pubescens,* not patented.

*Male, or pollen, parent.*—Unknown selection of *Syringa pubescens*, not patented.

Propagation:

*Type.*—By softwood cuttings.

*Time to initiate roots, summer.*—About 20 days at temperatures about 18C to 27C.

*Time to produce a rooted young plant, summer.*—About three months at temperatures about 18C to 27C.

*Root description.*—Fine, fibrous; typically white in color, actual color of the roots is dependent on substrate composition, water quality, fertilizer, substrate temperature and physiological age of roots.

*Rooting habit.*—Freely branching; dense.

Plant description:

*Plant form and growth habit.*—Perennial shrub; relatively compact, upright to outwardly spreading and mounding plant habit; moderately vigorous growth habit and moderate to rapid growth rate.

*Branching habit.*—Freely branching habit, about five to seven primary lateral branches develop per plant.

*Plant height.*—About 50 cm.

*Plant diameter* (*area of spread*).—About 35 cm.

Lateral branch description:

*Length.*—About 30 cm.

*Diameter.*—About 2 mm.

*Internode length.*—About 2.7 cm.

*Aspect.*—About 45 to 70 degrees from vertical.

*Strength.*—Strong.

*Texture.*—Initially slightly pubescent becoming smooth and glabrous with development.

*Color, developing.*—Close to 177B.

*Color, developed.*—Close to 177B; when woody, close to 199C.

Leaf description:

*Arrangement.*—Opposite, simple.

*Length.*—About 3.9 cm.

*Width.*—About 2.6 cm.

*Shape.*—Ovate.

*Apex.*—Acute.

*Base.*—Obtuse.

*Margin.*—Entire; slightly ciliate.

*Texture, upper surface.*—Smooth, glabrous.

*Texture, lower surface.*—Slightly pubescent.

*Venation pattern.*—Pinnate.

*Color.*—Developing leaves, upper surface: Close to 137B; at the edges, close to 177B. Developing leaves, lower surface: Close to 146B. Fully expanded leaves, upper surface: Close to 146A; venation, close to 146B. Fully expanded leaves, lower surface: Close to 146B; venation, close to 146B.

*Petioles.*—Length: About 5.7 mm. Diameter: About 1 mm. Texture, upper and lower surfaces: Pubescent. Color, upper surface: Close to 137B. Color, lower surface: Close to 137B tinged with close to 177B.

Flower description:

*Flower arrangement and flowering habit.*—Single salverform flowers arranged in dense terminal panicles; freely flowering habit with usually about 200 to 250 flowers developing per inflorescence; flowers face mostly upright to outwardly depending on position on inflorescence.

*Natural flowering season and flower longevity.*—Flowering remontant; plants of the new *Syringa* flower during the spring (April and May) and then again in the summer (July and August) in Michigan; flowers not persistent.

*Fragrance.*—Strongly fragrant; fragrance sweet, floral and pleasant with notes of rose and jasmine.

*Inflorescence height.*—About 7 cm.

*Inflorescence diameter.*—About 9 cm.

*Flower diameter.*—About 7 mm.

*Flower depth.*—About 1.2 cm.

*Flower throat diameter.*—About 2 mm.

*Flower tube length.*—About 1 cm.

*Flower tube diameter, proximally.*—About 1 mm.

*Flower buds* (*before showing color*).—Length: About 2 mm. Diameter: About 1 mm. Shape: Proximally, oblong and distally, orbicular. Color: Close to 144B and at the apices, close to 166A.

*Petals.*—Quantity and arrangement: Single whorl of four to five petals; lower portion of petals fused forming a narrow tube. Lobe length: About 3 mm. Lobe width: About 2 mm. Lobe shape: Elliptic. Apex: Acute. Margin: Entire. Texture, upper and lower surfaces: Smooth, glabrous; soft. Texture, throat and tube: Smooth, glabrous. Color: When opening, upper and lower surfaces: Close to 65A. Fully opened, upper surface: Close to 65D; color does not change with subsequent development. Fully opened, lower surface: Close to 65C; color does not change with subsequent development. Throat: Close to 70C. Tube: Close to 70C.

*Sepals.*—Quantity and arrangement: Single whorl of four small sepals; fused towards the base forming a campanulate-shaped calyx. Length: Less than 1 mm. Width: Less than 1 mm. Shape: Narrowly deltoid. Apex: Acute. Margin: Entire. Texture, upper and lower surfaces: Smooth, glabrous. Color, upper and lower surfaces: Close to 144B and at the apices, close to 166A.

*Peduncles.*—Length: About 5 cm. Diameter: About 2 mm. Strength: Strong. Aspect: About 45 degrees from the stem axis. Texture: Slightly pubescent. Color: Close to 200A.

*Pedicels.*—Length: About 1.5 cm. Diameter: About 1 mm. Strength: Strong. Aspect: About 45 degrees from peduncle axis. Texture: Slightly pubescent. Color: Close to 200A.

*Reproductive organs.*—Androecium: Quantity of stamens per flower: Two; filaments are adnate to the throat. Anther size: About 2 mm by 1 mm. Anther shape: Oblong. Anther color: Close to 8B. Amount of pollen: Abundant. Pollen color: Close to 8B. Gynoecium: Quantity of pistils per flower: One. Pistil length: About 1 mm. Stigma shape: Oblong. Stigma color: Close to 36C. Style length: About 1 mm. Style color: Close to 36C.

*Seeds and fruits.*—To date, seed and fruit development have not been observed on plants of the new *Syringa.*

Garden performance: Plants of the new *Syringa* have been observed to have good garden performance and to tolerate rain, wind and temperatures ranging from about −31C to about 38C.

Pathogen & pest resistance: To date, plants of the new *Syringa* have not been observed to be resistant to pathogens and pests common to *Syringa* plants.

It is claimed:

1. A new and distinct *Syringa* plant named 'SMNSPH' as illustrated and described.

* * * * *